(12) United States Patent
Correa et al.

(10) Patent No.: US 9,233,066 B2
(45) Date of Patent: Jan. 12, 2016

(54) ACTIVE FORMULATIONS BASED ON PLANT EXTRACTS; PHYTOCOSMETIC AND/OR PHYTOTHERAPEUTIC FORMULATIONS COMPRISING THE SAME METHOD FOR

(75) Inventors: Renilto Frota Correa, Manaus-AM (BR); Janaína Paolucci Sales, Manaus-AM (BR); Jaqueline De Araújo Bezerra, Manaus-AM (BR); Diego De Moura Rabelo, Manaus-AM (BR); Luiz Antonio De Oliveira, Manaus-AM (BR); Maria Lúcia Belém Pinheiro, Manaus-AM (BR); Silo Soares Da Silva, Manaus-AM (BR); Spartaco Astolfi Filho, Manaus-AM (BR)

(73) Assignee: Instituto Nacional de Pesquisa da Amazonia—INPA, Petropolis, Manaus (BR)

( * ) Notice: Subject to any disclaimer, the term of this patent is extended or adjusted under 35 U.S.C. 154(b) by 654 days.

(21) Appl. No.: 12/810,654
(22) PCT Filed: Dec. 28, 2007
(86) PCT No.: PCT/BR2007/000375
§ 371 (c)(1), (2), (4) Date: Jun. 25, 2010
(87) PCT Pub. No.: WO2009/082797
PCT Pub. Date: Jul. 9, 2009

(65) Prior Publication Data
US 2010/0284943 A1 Nov. 11, 2010

(51) Int. Cl.
A61K 8/97 (2006.01)
A61K 36/8905 (2006.01)
A61Q 11/00 (2006.01)
A01N 65/08 (2009.01)
A01N 65/40 (2009.01)
A61K 8/92 (2006.01)
A01N 65/00 (2009.01)
A61Q 17/00 (2006.01)
A61L 2/18 (2006.01)

(52) U.S. Cl.
CPC ............... *A61K 8/922* (2013.01); *A01N 65/00* (2013.01); *A01N 65/08* (2013.01); *A61K 8/97* (2013.01); *A61K 36/8905* (2013.01); *A61Q 11/00* (2013.01); *A61Q 17/005* (2013.01); *A61L 2/18* (2013.01)

(58) Field of Classification Search
CPC ....... A01N 65/00; A01N 65/08; A01N 65/40; A61K 36/8905; A61Q 11/00
See application file for complete search history.

(56) References Cited

PUBLICATIONS

Rao, VS et al. Natural Product Communications (2007); 2(12): 1199-1202. Compositio nand antinoceptive activity of the essential oil from Protium heptaphyllum resin.*
Wikipedia contributors, 'Burseraceae', Wikipedia, The Free Encyclopedia, Jun. 13, 2014, 19:04 UTC, <http://en.wikipedia.org/w/index.php?title=Burseraceae&oldid=612801373> [accessed Oct. 31, 2014].*
Siani, AC et al. Biochemical Systematics and Ecology, (2004); 32:477-489. Protium icicariba as a source of volatile essences.*
Bandeira, PN et al. Journal of Essential Oil Research (2001); 13(1):33-34.). Essential oil composition of leaves, fruits and resin of Protium heptaphyllum (Aubl.) March.*
Siani AC et al. J Ethnopharmacol. (1999); (1):57-69. Evaluation of anti-inflammatory-related activity of essential oils from the leaves and resin of species of Protium.*

* cited by examiner

*Primary Examiner* — Michele Flood
(74) *Attorney, Agent, or Firm* — Laurence P. Colton; Smith Risley Tempel Santos LLC

(57) ABSTRACT

Formulations with antibacterial and biofilm removing actions in which the formulations have at least one plant oil from a plant from the genus *Protium, Guatteria, Cyperus* in a suitable vehicle.

16 Claims, No Drawings

ACTIVE FORMULATIONS BASED ON PLANT EXTRACTS; PHYTOCOSMETIC AND/OR PHYTOTHERAPEUTIC FORMULATIONS COMPRISING THE SAME METHOD FOR

FIELD OF THE INVENTION

The present invention is directed to the use of an active formulation based on plant extracts, wherein said formulations possess plant extracts with antimicrobial and biofilm removing properties. The formulations of the present invention comprise at least one essential oil from plants selected from genus *Protium, Guatteria* and *Cyperus*, in a suitable vehicle. The present invention is directed to products related to the fields of dentistry, medicine, veterinary, personal hygiene, cleaning and pharmaceutical compositions for human and animal use.

BACKGROUND OF THE INVENTION

The antimicrobial properties of plant extracted substances are known due to its empirical use throughout the centuries and are being recently confirmed by science. Many researches, in several countries, including Brazil, owner of one of the world's largest biodiversity, were performed in view of the popular knowledge of the native species. Extracts and essential oils from some species were efficient in fighting microorganisms, such as filamentous fungi, yeast and bacteria. Some plants are described as possessing antimicrobial properties (such as antibacterial and antifungal) such as: olive tree (*Olea europaea*), sunflower (*Helianthus annuus*), andiroba (*carapa guianensis*), garlic (*Allium sativum*), sessile joyweed (*Althernanthera sessilis*) and some marine algae. These and other plants can be found in several countries besides Brazil, such as Cuba, India, Mexico and Jordan. Around the world, antimicrobial products are gaining special attention due to the increase in bacteria population resistance to conventional antibiotics; considering that no new class of antibiotics was discovered in the last years (1).

Certain chemical classes found in plants with antimicrobial activity (antibacterial and antifungal) can be cited such as terpenes and fenols (thymol, carvone, carvacrol, menthol and murolene) (2.3). Despite the fact that the mechanism of action of these substances is still unknown, there are clues that suggest that the action is associated with the lipophilic character of the compounds, which builds up in cell membranes, leading to a loss of energy of these cells (4,5)

Plants from several regions from Brazil possess other farmacological properties and have being used as natural medicines by local population, treating several tropical diseases, such as schistosomiasis, leishmaniasis, malaria and fungal and bacterial infections (6). Despite the vast biodiversity of Brazil, antimicrobial activity data is available only for 44 plant species from 20 families, including native and exotic species. Practical uses that can be suggested for these plants include phytotherapeutical products for human and animal use, as well as food industry and cleaning products.

The next paragraphs give details of patents and scientific papers related to products containing natural products with antimicrobial action using the plants of the present invention: *Protium, Guatteria, Cyperus* and *Aniba*.

The species *Protium heptaphyllum* March is a plant belonging to genus *Protium* and to the family Burseraceae, native in Brazilian cerrado. Some genus of this family (*Elaphrium, Icica, Canarium* and *Protium*) are producers of oily resins also known as "elemi". Siani et al. (10) describe the essential oils extracted from the leaves and the resins from *Protium* species as having anti-inflammatory activity, but a product containing said essential oils has not been suggested.

No document in patent literature regarding the use of *Protium* plants for the purposes herein described was found.

Document US 2007/0166255 describes a formulation containing natural lignans for topical use in the prevention and treatment of sunburns and wounds. These lignans are found as conjugated glycosides in several parts of plants of several genus, being associated to fibers, specially in conifers.

Plants from genus *Guatteria* belongs to family Annonaceae, dicotyledons from Magnoliales order. This group includes several fruits used as foods such as soursop (*Annona muricata*), fruta-do-conde (*Annona coriaceae*) and sugarapple (*Annona squamosa*). *Guatteria citriodora* Ducke, also known as laranjinha or laranjeirinha, is a tree from this family, native from Amazon region of Brazil. *Guatteria* genus plants have been described in scientific papers containing antileishmanial and antimalarial activity.

The patent literature contains few documents related to *Guatteria* plants.

In documents WO 04/084801 and WO 05/035783, these plants are cited for treatment of leishmaniasis. It is known that this plant contain aporphinic alkaloids, an alkaloid subclass, described in these documents as useful for both visceral and cutaneous leishmaniasis, in both animals and humans.

Document US 2005/0181077 describes the use of this genus and the discover of medicines. In this document, two families used in the present invention, namely Annonaceae and Cyperaceae are suggested; however, only the genus *Guatteria* is suggested in the present invention. There is no suggestion of the possibility of using plants from *Cyperus* genus, unlike the present invention. The pharmaceutical formulation proposed is aimed to the treatment of AIDS while the present invention is not.

Documents WO 03/08278 and U.S. Pat. No. 6,590,127 suggest the use of *Guatteria gaumeri* in the preparation of a pharmaceutical formulation useful in treating hypercholesterolemia.

No document in patent literature regarding the use of *Guatteria citriodora* for the purposes herein described was found.

*Aniba roseodora* Ducke, also known as rosewood, is a 30-meter tall tree that can be found in north and western Amazon, specially in the states of Amazônia, Pará and Amapá.

Documents U.S. Pat. Nos. 7,150,888, 7,048,953 and US 2004/0009245 disclose antibacterial activity of *Aniba roseodora* essential oil. In these documents is suggested the inhalation of essential oil vapors for antibacterial effects in the respiratory tract. In the abovementioned documents there is no suggestion of spray formulations for skin wounds.

Document WO 05/087244 describes a pharmaceutical formulation with antimicrobial activity containing at least two essential oils, derived from several genus of plants, including *Aniba*, and more specifically *Aniba roseodora*, also used in the present invention. The antimicrobial activity aimed in this document in antifungal, while the present invention is not.

Document U.S. Pat. No. 7,060,306 described a formulation for treatment and relief of skin disorders such as dermatitis, psoriasis, cutaneous rash. In the formulation disclosed, the essential oil of 11 natural agents, such as karate butter, mango butter, beeswax, chamomile, carrot seed oil, rosemary oil, cedar wood oil, pau-rosa oil, rose fruits oil, grapefruit seed extract and sweet orange oil, are suggested in formulations of lotions or soaps for treatment of skin disorders. The genus used in the present invention, namely *Cyperus, Guatteria, Protium* or *Aniba*, have not been cited in this document.

The use of *Aniba* extract is also suggested in documents EP 1 239 735 and Wo 06/101409, respectively, regarding formulations related to insecticide activity and a cosmetic formulation, including a skin spray formulation. However, document WO 06/101409 does not mention the simultaneous use of *Protium* and *Guatteria* species.

No document related to the use of essential oils obtained from *Aniba* plants in disinfectant formulations was found.

The remaining genus used in the present invention, *Cyperus*, belongs to Cyperaceae family, which includes about 600 species of aquatic plants, that can be found in tropical and temperate zones of all continents. This genus is known as one of the most invasive weeds known, being allelophatic, i.e. its roots release harmful substances to other plants. It is used in alternative medicine to treat sickness, fever, inflammation and pain.

Several patents disclose *Cyperus* plants. Document WO 06/117516 discloses a formulation with antibacterial activity for topic use useful for treating infections caused by microorganisms, such as *Escherichia coli*, in which the species *Cyperus esculentus* is used. This document still suggests that *C. esculentus* extracts can be used alone or in combination with other essential oils in aromatherapy. No reference was found regarding the use of *Cyperus rotundus* Linn.

Document WO 06/096239 describes the use of *Cyperus* plants as part of a antimicrobial formulation used to provide skin benefits. Like WO 06/117516, this plant's extract is used as a natural oil optionally included to provide fragrance.

Documents U.S. Pat. Nos. 4,569,843 and 4,696,818 reveal a method for treatment of drug abuse comprising oral administration of a herbal formulation, containing *Radiz angelica sinensis*, *Herba pogostemi*, *Cyperus rotundus* and *Squama manitis* pendactilae. Document U.S. Pat. No. 4,826,684 reveals a production process of a composition for use in insulin-dependent diabetes treatment. The main active is a mixture of terpenes from *Cyperus rotundus* Linn, being orally administered. Document U.S. Pat. No. 5,476,651 reveals the use of a extract of *Cyperus rotundus* Linn in the preparation of a cosmetic or pharmaceutical composition for the promotion of skin and hair pigmentation or for treatment of pigmentation disorders. Such documents propose different uses and formulations when compared with the present invention, i.e. the technical problems solved are different, as well as the technical solutions proposed therein.

Document U.S. Pat. No. 5,906,825 describes the use of *Cyperus* plant extracts as part of polymers comprising antimicrobial agents and methods for production of them. This plant is described as a phytochemical that can be added to a product as a biocidal agent (expression used collectively for disinfectants, chemical sterilizers, antiseptic and preservatives). The abovementioned document does not anticipates or overlap with the present invention, since essential oils of *Protium* and/or *Guatteria* plants are not used.

The scientific literature listed below, related to the prior art, does neither anticipates nor suggests, directly or indirectly, any of the objects of the present invention.

1 BAQUERO F, BLÁZQUEZ J (1997) Tree 12:482-487
2 SMID E J, KOEKEN J P G, GORRIS L G M (1996) In: Modern Fungicides and Antimicrobial Compounds, Lyr H., Russell P E, Sisler H D Eds., Intercept: Andover, UK, 173-180
3 HELANDER I M, ALAKOMI H L, LATVA-KALA K, MATTILA-SANDHOLM T, POL I, SMID E J, GORRIS L G M, VON WRIGHT, A (1998) *J. Agric. Food Chem.* 46:3590-3595
4 CONNER D E (1993) In: Antimicrobials and Foods, Davidson P M, Branem A L Eds, Dekker: New York, 441-468
5 SIKKEMA J, D E BONT J A M, POOLMAN B (1995) *Microbiology Reviews* 59:201-222
6 ALVES, T M A, SILVA A F, BRANDÃO M, GRANDI T S M, SMÂNIA E F, SMÂNIA J Á, ZANI C L (2000) *Mem. Inst. Oswaldo Cruz* 95:367-373
7 MONTENEGRO H, GUTIERREZ M, ROMERO L I, ORTEGA-BARRIA E, CAPSON T L, CUBILLA RIOS L (2003) Aporphine alkaloids from *Guatteria* spp. with leishmanicidal activity. Planta medica, 69: 677-679.
8 FISHER D C, DE AMORIM GUALDA N C, BACHIEGA D, CARVALHO C S, LUPO F N, BONOTTO S V, ALVES O, YOGI A, SANTI S M, AVILA P E, KIRCHGATTER K, MORENO PR. *Acta Trop.* 2004 November-December; 92(3):261-6
9 WENIGER B, ARAGON R, DEHARO E, BASTIDA J, CODINA C, LOBSTEIN A, ANTON R. *Pharmazie*. 2000 November; 55(11):867-8
10 SIANI, A C; RAMOS, M F S; LIMA, O M; SANTOS, R R; FERREIRA, E F; SOARES, R O A.; ROSAS, E C; SUSUNAGA, G S; GUIMARÃES, A C; ZOGHBI, M G B, HENRIQUES, M G M O *J. Ethnopharmacol.*, 1999, 47; 890-892

In summary, the present invention provides a new combination of natural agents with antimicrobial and biofilm removing properties. This combination, which includes necessarily essential oils from plants belonging to genus *Cyperus* and/or *Guatteria* and/or *Protium* and, at least, the essential oil of plants from other (or the same) genus, being the preferred genus in the present invention the genus *Aniba*. As described above, formulations containing this combination of essential oils with this type of action are unknown.

OBJECTS OF THE INVENTION

The present invention has as main innovation an active formulation based on plant extracts.

It is an object of the present invention an active formulation based on plant extracts comprising:
a) at least one essential oil from plants selected from the group which comprises the *Protium*, *Guatteria*, *Cyperus* genus and mixtures thereof;
b) a suitable vehicle.

Advantageously, the essential oils from a) can be obtained from any part of the plant, as stem, flowers, fruits, leafs, branches, seeds and roots. In one preferred embodiment, the selected plants are *Protium heptaphyllum* March, *Guatteria citriodora* Ducke and/or *Cyperus rotundus* Linn.

In another embodiment, the formulation additionally comprises an essential oil from plants selected from the group which comprises plants from *Aniba* genus.

In one advantageous embodiment, the selected plants are *Aniba roseodora* Ducke and an essential oil which can be obtained from any part of the plant as stem, flowers, fruits, leafs, branches, seeds and roots.

The present invention also provides products with biofilm removing and antimicrobial properties, wherein such products comprise the active formulation and other ingredients. Specially, the product is a phytotherapeutical and/or cosmetic and provides a formulation directed to products related to the fields of dentistry, medicine, veterinary, personal hygiene, cleaning and pharmaceutical compositions for human and animal use.

The products related to personal hygiene comprise phytotherapeutical formulations for toothpastes, dental cream, dental gel, oral rinse, prophylactic cream, liquid soaps, glycerinated soaps, calcium hydroxy pastes, healing spray, surfaces oil-based disinfectants and toothbrushes, prosthesis and orthodontic retainers. More specifically, the present invention provides formulations for these products.

The formulation of the present invention can be used in hair care products as shampoos, conditioners, relaxing, highlightning, hair-styling gel, fixing gel, spray mousses, hair styling creams, mousses, hair coloring products (temporary or permanent) and in skin care products such as shaving creams, after-shave lotions, sunscreens, creams, ointments, liquid soaps, bar soaps.

The pharmaceutical formulations are chosen from the group comprising spray, ointment, gel, among others. In one preferred embodiment, the present invention relates to a spray formulation.

The cleaning compositions of the present invention are chosen from the group comprising disinfectants, detergents, heavy duty cleaning products, etc.

In a preferred embodiment, the present invention provides products, detailed in the following tables, comprising the essential oils described above having biofilm removing and antibacterial properties.

These and other objects of the invention will be better understood from the detailed description of the invention.

DETAILED DESCRIPTION OF THE INVENTION

The following examples are illustrative of the present invention and are by no means intended to limit the scope of the present invention.

Several variants of the present invention can be prepared from the teaching of the present invention, mainly depending on the intending formulation action. For oral hygiene products, the inventors of the present invention suggest a preferred formulation containing the essential oil from a plant from genus *Protium*, a plant from genus *Guatteria* and a plant from genus *Cyperus*. For formulations related to personal hygiene products, a preferred formulation containing the essential oil from a plant from genus *Protium* and a plant from genus *Guatteria*. The prophylactic formulation for treatment of skin disorders comprises, besides essential oils from plants from genus *Protium* and *Guatteria*, essential oils from plants from genus *Aniba*. For general cleaning products, preferred formulations are made with essential oils from a plant from genus *Guatteria* and a plant from genus *Aniba*.

The present invention provides a formulation comprising:
a) at least one essential oil selected from the group which comprises the *Protium, Guatteria, Cyperus* genus and mixtures thereof;
b) a suitable vehicle.

In another embodiment, the formulation comprises an essential oil of a plant selected from the group consisting of *Aniba* genus.

Essential Oils

The essential oils referred herein are oils with antimicrobial, wound healing, biofilm removing and/or fixative activity. Useful plants to be used in the present invention include, but are not limited to:
plants of *Protium* genus, specially *Protium heptaphyllum* March; (with wound healing properties);
plants of *Guatteria* genus, specially *Guatteria citriodora* Ducke; (with antimicrobial properties);
plants of *Cyperus* genus, specially *Cyperus rotundus* Linn; (with biofilm removing properties); and
plants of *Aniba* genus, specially *Aniba roseodora* Ducke; (with fixative proprieties)

The essential oils of the abovementioned plants can be obtained from any part of the plants including, but not limited to stem, flowers, fruits, leafs, branches, seeds and roots. The extraction can be done through usual state of art methods. The essential oils can be present in a range comprising from 0.01% w/w to 3.0% w/w, depending on the product used. The most preferred ranges according to the present invention are:

1—Phytotherapic dental gel, comprising from 0.02% w/w to 0.1% w/w.

2—Phytotherapic dental cream with Fluor, comprising from 0.02% w/w to 0.1% w/w.

3—Phytotherapic cream with calcium hydroxy, comprising 0.5% w/w to 1.0% w/w.

4—Phytotherapic prophylactic cream with Fluor, comprising 0.02% w/w to 0.1% w/w.

5—Phytotherapic oral rinse, comprising from 0.02% w/w to 0.1% w/w.

6—Phytotherapic glycerin soap, antibacterial and wound healing, comprising from 0.01% w/w to 0.02% w/w.

7—Phytotherapic antibacterial and wound healing liquid soap, comprising from 0.2% w/w to 0.3% w/w.

8—Liquid disinfectant with Amazon oils comprising at least two essential oils, wherein the first oil comprises from 0.1% w/w to 0.3% w/w and the second oil comprises from 1.5% w/w to 3.0% w/w.

9—Prophylactic antimicrobial and wound healing spray, comprising from 0.03% w/w to 0.4% w/w.

10—Toothbrushes, dental prosthesis and orthodontic retainers disinfectant, comprising from 0.02% w/w to 0.1% w/w Specially, the oil from *Cyperus rotundus* Linn is preferably used in the formulation of products for biofilm removal. In the same way, the oils from *Guatteria citriodora* Ducke and *Protium heptaphyllum* March presents anti-septic and antimicrobial activity against oral bacteria.

The present invention provides several other compounds described in the classes below. A person skilled in the art will understand that any compound belonging to the state of the art and to the following classes is useful in the preparation of formulations according to this invention. The following compounds are examples of suitable compounds and are, by no means, intended to limit the scope of the present invention.

Surfactant Agent

Preferred surfactants for the present invention are chosen from the groups comprising anionic surfactants, nonionic surfactants, cationic surfactants and amphoteric/zwitterionic surfactants.

Suitable anionic surfactants that can be used in the present invention include, but are not limited to, alkaline and/or alkaline earth metals salts of fatty acids, alkyl sulfates ammonium salts, ethoxylated alkyl sulfates, alkyl sulfonates, akyaryl sulfonates, alkyl sulfosuccinate, alkyl ether sulfosuccinate, alkyl sulfosuccinamate, alkyl amide sulfosuccinate, alkyl carboxilate, alkyl succinate, ether alkyl carboxilate. The alkyl or acyl groups present have a carbonic chain from about 12 to about 20 carbon atoms. The aryl group has a phenyl or benzyl group.

Suitable non-ionic surfactants that can be used in the present invention include, but are not limited to, ethoxylated alcohol with linear alcohol groups of natural origin with from 12 to 18 carbon atoms and an average of 2 to 8 EO by mol of alcohol.

The fatty alcohols with more than 12 EO can also be used. Alkyl glycosides can be added if it satisfies the general formula RO(G)x, wherein R is a primary or methyl branched linear group, particularly 2-methyl branched. This aliphatic group contains from 8 to 22 carbon atoms, more preferably from 12 to 18 carbon atoms. G can be an glycosidic unit containing from 5 to 6 carbon atoms, preferably glucose. The oligomerization degree x, which defines the distribution of monoglycosides and oligoglycosides is a number between 1 and 10.

Non-ionic surfactants like amine oxide such as N-cocoalkyl-N,N-dimethylamine oxide and N-tallow alkyl-N,N-dihydroxyethylamine oxide and fatty acids alkanolamides are also suitable to be used at the present invention.

Amphoteric/zwitterionic surfactants can be extensively described as secondary and tertiary amines derivatives or quaternary ammonium derivatives, quaternary phosphonium derivatives or tertiary compounds of sulfonium. The cationic atom of the quaternary compound can be part of a heterocyclic ring. All these compounds have at least one aliphatic group, linear or branched, having from about 3 to about 18 carbon atoms and at least one aliphatic substituent having an anionic group, water-soluble, i.e. carboxy, sulfonate, sulfate, phosphate or phosphono. Examples of suitable zwitterionic surfactants that can be used at the present invention are described herein below.

Amphocarboxylates, alkyl betaines, amidoalkyl betaines, amidoalkyl sultaines, amphophosphates and phophosbetaines.

The surfactant agent can be present in a range comprising from 0.1% w/w to 25% w/w depending upon the intended product. The most common ranges are listed here:

1—Phytotherapic dental gel, comprising from 0.8% w/w to 1.5% w/w;
2—Phytotherapic cream with Fluor, comprising from 0.8% w/w to 1.5% w/w;
3—Phytotherapic and prophylactic cream with Fluor, comprising 0.8% w/w to 1.2% w/w;
4—Phytotherapic oral rinse, comprising from 0.1% w/w to 0.7% w/w;
5—Phytotherapic antibacterial and wound healing glycerin soap, comprising from 1.5% w/w to 2.5% w/w;
6—Phytotherapic antibacterial and wound healing liquid soap, comprising two surfactant agents, one from 0.8% w/w to 1.2% w/w and the other from 18% w/w to 25% w/w;
7—Disinfectant with Amazon oils, comprising from 2.0% w/w to 3.5% w/w
8—Prophylactic antimicrobial and wound healing spray, comprising from 0.1% w/w to 0.4% w/w;
9—Disinfectant for toothbrushes, dental prosthesis and orthodontic retainers, comprising from 0.1% w/w to 0.5% w/w;

Thickening Agent

Suitable thickening agents according to the present invention include, without limitation, carboxylic acid/carboxylate copolymers such as hydrophobically-modified cross-linked copolymers of carboxylic acid and alkyl carboxylate.

Additional viscosity modifiers useful herein are vinyl polymers such as cross linked acrylic acid polymers, such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch (rice, corn, potato, wheat), algae colloids (algae extract), starch-based polymers such as carboxymethyl starch, methylhydroxypropyl starch, alginic acid-based polymers such as propylene glycol esters, sodium polyacrylate, polyethylacrylate, polyacrylamide, polyethyleneimine, and inorganic water soluble material such as bentonite, aluminum magnesium silicate, laponite, hectonite, and anhydrous silicic acid.

The thickening agent can be present in a range comprising from 0.3% w/w to 52% w/w depending upon the intended product. The most common ranges are listed here:

1—Phytotherapic dental gel, comprising from 0.3% w/w to 0.7% w/w.
2—Phytotherapic dental cream with Fluor, comprising from 0.3% w/w to 0.8% w/w.
3—Phytotherapic and prophylactic cream with Fluor, comprising from 48% w/w to 52% w/w.
4—Phytotherapic antibacterial and wound healing glycerin soap, comprising from 1.0% w/w to 2.0% w/w.
5—Phytotherapic antibacterial and wound healing liquid soap, comprising from 0.5% w/w to 3.5% w/w.

Humectant Agent

Useful humectant agents of the present invention include, without limitation:

a) water-soluble liquid polyols as for example glycerin, propylene glycol, hexylene glycol, buylene glycol, and dipropylene glycol;
b) polyethylene glycol of the formula:

$$HO\text{---}(RO)n\text{-}H$$

wherein R is an alkyl group with 2 or 3 carbon atoms and n is 2 to 10;
c) methyl glycosides polyethylene glycol ethers;
d) urea The humectant agent can be present in a range that comprises from 0.5% w/w to 99% w/w, depending upon the intended product. The most common ranges are listed here:

1—Phytotherapic dental gel comprising from 20% w/w to 25% w/w;
2—Phytotherapic dental cream with Fluor comprising from 20% w/w to 25% w/w
3—Phytotherapic and prophylactic cream with Fluor comprising two humectant agents in which one of them comprising from 4.0% w/w to 6.0% w/w and the other from 14% w/w to 17% w/w.
4—Phytotherapic oral rinse comprising from 20% w/w to 25% w/w
5—Phytotherapic antibacterial and wound healing glycerin soap, comprising from 1.0% w/w to 2.0% w/w.
6—Phytotherapic antibacterial and wound healing liquid soap, comprising 0.5% w/w to 1.5% w/w.
7—Prophylactic antimicrobial and wound healing spray, comprising from 97% w/w to 99% w/w.
8—Disinfectant for toothbrushes, dental prosthesis and orthodontic retainers, comprising from 20% w/w to 25% w/w.

Abrasive Agents

The abrasive agent used in the present invention is chosen from the group that comprises, without limitation, pomme stone, alumina, silica, alkaline and alkaline earth metal phosphate, such as ortho- meta- and pyrophosphates, carbonates and/or silicates salts such as calcium carbonate, magnesium carbonate, calcium pyrophosphate, calcium phosphate, alkaline metals metaphosphates, magnesium phosphates, magnesium silicate, calcium meta silicate.

In a preferred embodiment the present invention uses calcium pyrophosphate, calcium carbonate, pomme stone and/or dehydrated calcium phosphate.

The abrasive agent can be present in a range that comprises from 17% w/w to 50% w/w, depending upon the intended product. The most common ranges are listed here:

1—Phytotherapic dental gel, comprising from 45% w/w to 50% w/w.
2—Phytotherapic cream with Fluor, comprising from 42% w/w to 47% w/w.

3—Phytotherapic and prophylactic cream with Fluor comprising from 17% w/w to 18% w/w.

Antimicrobial Agent

The antimicrobial agent used in the present invention is chosen from the group that comprises, without limitation, antimicrobial agents such as tertiary amines with a fatty alkyl group of 12 to 18 carbon atoms and optionally, two (poly) oxyethylenes attached to the nitrogen, quaternary ammonium, compounds such as benzethonium chloride or quaternary ammonium halides such as dodecyl-, tetradecyl- and hexadecyltrimethyl ammonium halides. Other compounds such as methyl, ethyl, buthyl, propyl and isobutyl parabens can also be used.

The antimicrobial agents used in the present invention are also chosen from the group that comprises plant extracts such as essential oils. Suitable plants are selected from the group that comprises plants from the genus *Guatteria* and/or *Protium* and/or *Cyperus*, more specifically *Guatteria citriodora* Ducke, *Protium heptaphyllum* March and *Cyperus rotundus* Linn.

The antimicrobial agent can be present in a range that comprises from 0.01% w/w to 92% w/w, depending upon the intended product. The most common ranges are listed here:

1—Phytotherapic dental gel comprising from 0.02% w/w to 0.5% w/w.

2—Phytotherapic dental cream with Fluor comprising from 0.02% w/w to 0.1% w/w.

3—Prophylatic phytotherapic paste with calcium hydroxide comprising two antimicrobial agents, one from 0.5% w/w to 1.0% w/w and the other from 88% w/w to 92% w/w.

4—Phytotherapic and prophylactic cream with Fluor comprising from 0.01% w/w to 0.3% w/w.

5—Phytotherapic oral rinse that comprises from 0.02% w/w to 0.1% w/w.

6—Phytotherapic antibacterial and wound healing glycerin soap, comprising from 0.01% w/w to 0.02% w/w.

7—Phytotherapic antibacterial and wound healing liquid soap, comprising from 0.04% w/w to 0.4% w/w.

8—Disinfectant with Amazon oils, comprising from 2.0% w/w to 3.0% w/w.

9—Prophylactic antimicrobial and wound healing spray, comprising from 0.02% w/w to 0.3% w/w;

10—Disinfectant for toothbrushes, dental prosthesis and orthodontic retainers, comprising from 0.02% w/w to 0.1% w/w;

Biofilm Removing Agent

The biofilm removing agent used in the present invention is chosen from the group that comprises the plant extracts such as essentials oils. The selected plant belongs to the genus *Cyperus*, specifically *Cyperus rotundus* Linn.

The biofilm removing agent is preferably present in a range that comprises from 0.05% w/w to 1.3% w/w, depending upon the intended product. The most common ranges are listed here:

1—Phytotherapic dental gel comprising from 0.05% w/w to 0.15% w/w;

2—Phytotherapic dental cream with Fluor comprising from 0.05% w/w to 0.15% w/w;

3—Phytotherapic paste from calcium hydroxide comprising from 0.8% w/w to 1.3% w/w;

4—Phytotherapic paste with Fluor comprising from 0.05% w/w to 0.15% w/w;

5—Phytotherapic oral rinse comprising from 0.05% w/w to 0.15% w/w; and 6—Disinfectant for toothbrushes, dental prosthesis and orthodontic retainers comprising from 0.05% w/w to 0.15% w/w.

Antimicrobial Fixer Agent

The antimicrobial fixer agent used in the present invention is chosen from the group that comprises plant extracts such as essential oils. The plant selected belongs to the genus *Aniba*, specifically *Aniba roseodora* Ducke.

The antimicrobial fixer agent is preferentially in a range that comprises from 0.1% w/w a 0.4% w/w, depending upon the intended product. The most common ranges are listed here:

1—Disinfectant with Amazon oils comprising from 0.1% w/w to 0.3% w/w; and

2—Prophylatic antimicrobial and wound healing spray comprising from 0.2% w/w to 0.4% w/w.

Fluor Based Compounds

The Fluor based compound is chosen from the group comprising the chemical compounds that are fluoride sources such as monofluorophosphates salts such as sodium monofluorophosphates, lithium monofluorophosphate, potassium monofluorophosphate, ammonium monofluorophosphate or mixtures thereof. Other suitable compounds include fluorides such as sodium and potassium fluorides.

The Fluor based compounds can be present in a range that comprises from 900 to 1600 ppm, depending upon the intended product. The most common ranges are listed here:

1—Phytotherapic dental gel comprising from 900 ppm to 1100 ppm of sodium monofluorophosphate;

2—Phytotherapic dental cream with Fluor comprising from 1.400 ppm to 1600 ppm of sodium monofluorophosphate;

3—Phytotherapic and prophylactic cream with Fluor comprising from 1.400 ppm to 1600 ppm of sodium monofluorophosphate.

Optional Components

The compositions of the present invention can comprise also optional components as flavouring agents, enzymes, fragrance, pigments, colorants, preservatives, pH regulators, propelants, antioxidants (BHT, BHA), chelants (EDTA, EGTA, among others), bactericides, fungicides, antiviral agents, opacifying agents, bleach agents, conditioning polymers, silicone, among others.

Below are some examples of applications of these formulations. These examples do not limit the scope of the invention, but only illustrates some of the several forms of use. Further, the preparation methods of all formulations described here comprises the general used process described in the state of the art.

EXAMPLE 1

Essential Oils

The extraction of vegetal volatiles oils from the species: tiririca (*Cyperus rotundus* Linn), breu-branco (*Protium heptaphyllum* March), pau rosa (*Aniba roseodora* Ducke), and laranjinha (*Guatteria citriodora* Ducke) is described below.

The crushed and dried botanic material is placed in a 1 to 5 L volumetric flask according to the ratio botanic material: water 1:10. The essential oil extraction is performed by steam stripping and the difference in density allows the recovery of the plant extract through hydrodistillation, in the Clevenger system for 2 to 3 hours, keeping the temperature of 100° C. After that, the oils are dried using anhydrous $Na_2SO_4$. The essential oil is then stored in amber flask and kept refrigerated for conservation to avoid loss of constituents.

EXAMPLE 2

Formulation for Dental Gel

In a preferred embodiment of the present invention, the formulation for a dental gel with essential oils comprises the compounds according to the following Tables 1 and 2.

TABLE 1

Dental gel formulation
Phytotherapic dental gel with Fluor

| | |
|---|---|
| Cyperus rotundas Linn oil | 0.1 mL |
| Guatteria citriodora Ducke oil | 0.02 mL |
| Protium heptaphyllum March oil | 0.05 mL |
| Fluoride (MFP-Na$_2$) | 1000 ppm |
| Dental gel vehicle | To 100 g |

TABLE 2

Formulation for the dental gel vehicle

| | |
|---|---|
| Glycerin | 22 g |
| Carbopol 934 | 500 mg |
| Destilled water | 25.19 mL |
| Tetrasodium pyrophosphate | 250 mg |
| Sodium saccharin | 200 mg |
| Sodium benzoate | 500 mg |
| Sodium hydroxide solution 50% | 0.4 mL |
| Calcium phosphate dihydrated | 48.76 g |
| Lauryl sodium sulphate | 1-2 g |
| Flavouring | 1 mL |

EXAMPLE 3

Dental Cream Formulation

In a special embodiment of the present invention, the dental cream formulation with essential oils comprises the compounds according to the following Tables 3 and 4.

TABLE 3

Dental cream formulation
Phytotherapic dental cream with Fluor

| | |
|---|---|
| Cyperus rotundus Linn. oil | 0.1 mL |
| Guatteria citriodora Ducke oil | 0.02 mL |
| Protium heptaphyllum March oil | 0.05 mL |
| Fluoride (in MFP-Na$_2$ form) | 1500 ppm |
| Dental cream vehicle | To 100 g |

TABLE 4

Formulation for dental cream vehicle
Vehicle to dental creams

| | |
|---|---|
| Calcium pyrophosphate | 45 g |
| Sorbitol solution 70% | 20 mL |
| Lauryl sodium sulphate | 1.2 g |
| Carboxymethylcellulose | 600 mg |
| Sodium saccharin | 100 mg |
| Flavouring (menthol oil) | 0.75 mL |
| Water | 32.35 mL |

EXAMPLE 4

Dentistry Paste Formulation

It is indicated to dentistry use, specifically in the endodontics field (root canal treatment) as calcium hydroxide paste with antimicrobial and antiseptic action from the *Guatteria citriodora* Ducke oil, wound healing action from the *Protium heptaphyllum* March oil and biofilm removing action from *Cyperus rotundus* Linn oil being used as intracanal drug in teeth with exudates and lateral and apical root reabsorptions. These oils were scientifically tested and the properties confirmed. The product aims the removal of intracanal biofilm chemically formed in the human teeth as well as present wound healing, antimicrobial and antiseptic activities against endodontic bacteria. The formulation presented below comprises a ratio of 10 mL liquid to each 12 g powder.

In a special embodiment of the present invention, the dentistry paste formulation with the essential oils comprises the compounds according to the following Tables 5 and 6.

TABLE 5

Dentistry paste powder formulation

| | |
|---|---|
| Calcium hydroxide | 90% |
| Bismute carbonate | 10% |

TABLE 6

Dentistry phytotherapic paste liquid formulation

| | |
|---|---|
| Cyperus rotundas Linn oil | 0.1 mL |
| Guatteria citriodora Ducke oil | 0.05 mL |
| Protium heptaphyllum March oil | 0.05 mL |
| Olive oil | To 10 g |

EXAMPLE 5

Prophylatic Paste with Fluor Formulation

The prophylatic paste with Fluor presents antimicrobial and biofilm removing action since it uses the essential oil from *Cyperus rotundus* Linn as a remover of the biofilm formed by *Streptococcus mutans*, the main bacteria that causes dental caries in humans, and the essential oil from *Guatteria citriodora* Ducke that has action as oral antimicrobial and anti-septic and the essential oil from *Protium heptaphyllum* March that has wound healing action in oral cavity. These oils were scientifically tested and the biofilm removing, antimicrobial and wound healing actions were confirmed. It allows the interruption of the carious process making easy the process of cleaning, and removing detritus and spots as well as prevents the dental caries formation, wounds in the oral cavity and periodontal diseases.

In a special embodiment of the present invention, the formulation of the prophylatic paste with the essential oils comprises the compounds according to the following Tables 7, 8 and 9.

TABLE 7

Formulation of prophylatic phytotherapic paste with Fluor

| | |
|---|---|
| Cyperus rotundas Linn oil | 0.1 mL |
| Guatteria citriodora Ducke oil | 0.02 mL |

TABLE 7-continued

Formulation of prophylatic phytotherapic paste with Fluor

| | |
|---|---|
| *Protium heptaphyllum* March oil | 0.05 mL |
| Fluoride (in MFP-Na$_2$ form) | 1500 ppm |
| Prophylatic base paste | To 100 g |

TABELA 8

Formulation of prophylatic base paste

| | |
|---|---|
| Calcium carbonate | 35 g |
| Glycerin | 30 g |
| Nipagin | 0.1% |
| Sodium saccharin | 0.2% |
| Menthol | 0.3% |
| Mint essence | s.q. |
| Lauryl sodium sulphate (powder) | 1.0% |
| Natrosol gel 2.0% | To 100 g |
| Pomme stone | 35 g |
| Destilled water | To 30 mL |

TABLE 9

Formulation of natrosol gel

| | |
|---|---|
| Natrosol | 2% |
| Nipagin | 0.1% |
| Propylene glycol | 5% |
| EDTA | 0.1% |
| Water | To 100 mL |
| Phenonip | 0.05% |

EXAMPLE 6

Mouth Rinse Formulation

The phytotherapic mouth rinse with antimicrobial, antiseptic, wound healing and biofilm removing action uses the essential oil of *Cyperus rotundus* Linn as remover for biofilm caused by *Streptococcus mutans*, the main bacteria that causes the dental caries in humans, as well as the essential oil of *Guatteria citriodora* Ducke as oral antimicrobial and antiseptic and the essential oil of *Protium heptaphyllum* March that presents antimicrobial and wound healing action in the oral cavity. These oils were scientifically tested and the antimicrobial, wound healing and biofilm removing properties confirmed as well as the prevention of dental caries formation.

In a special embodiment of the present invention, the formulation of mouth rinse with essential oils comprises the compounds according to the following Table 10.

TABLE 10

Mouth rinse formulation

| | |
|---|---|
| Cetylpyridinium chloride | 100 mg |
| Citric acid | 100 mg |
| *Cyperus rotundas* Linn oil | 0.1 mL |
| *Guatteria citriodora* Ducke oil | 0.02 mL |
| *Protium heptaphyllum* March oil | 0.05 mL |
| Polysorbate 60 | 0.3 mL |
| Ethanol 95% | 10 mL |
| Sorbitol solution 70% | 20 mL |
| Water | To 100 mL |

EXAMPLE 7

Formulation for Glycerined Soap

The phytotherapic glycerinated soap with bactericidal and wound healing properties uses essential oil from *Guatteria citriodora* Ducke with antimicrobial and antiseptic properties and the oil from *Protium heptaphyllum* March with wound healing action. If used in a continuous form, it helps in the cleaning, and wound healing process and also prevents diseases produced by bacteria found in the skin.

In a special embodiment of the present invention, the formulation for glicerined soap with essential oils comprises the compounds according to the following Table 11.

TABLE 11

Antimicrobial and wound healing glycerined soap.

| | |
|---|---|
| Cocconut fat (babaçu cocconut oil) | 4.5 Kg |
| Castor oil | 1 Kg |
| Odourless and clarified industrial fat matter (½ stearic acid known as double or triple action stearin). | ½ Kg |
| Soda 99 (or 2 kg liquid soda) | 1 Kg |
| Álcohol without additives | 4 L |
| Water | 2 L |
| Refined sugar | 1 kg |
| Tetrasodic EDTA | 12 g |
| BHT | 12 g |
| Glycerin | 200 g |
| Propylene glycol | 200 g |
| Lauryl sodium sulphate | 300 mL |
| Synthetic amide (amide 90) | 200 mL |
| *Guatteria citriodora* Ducke oil | 2.5 mL |
| *Protium heptaphyllum* March oil | 2.5 mL |

EXAMPLE 8

Formulation for Liquid Soap

The liquid phytotherapic soap with antimicrobial and wound healing properties is recommended as prophylactic in the hands and wounds cleaning.

In a special embodiment of the present invention, the liquid soap formulation with essential oils comprises the compounds according to the following Table 12.

TABLE 12

Antimicrobial and wound healing phytotherapic liquid soap

| | | |
|---|---|---|
| Phase A | Lauryl ether sodium sulphate | 200 mL |
| | Zonen MI | 0.5 mL |
| | Propylene glycol | 10 mL |
| | Sunquart ® SC-50 | 10 mL |
| | Cocconut diethanolamyde | 30 mL |
| | Glucamate DOE | 7 g |
| | Citric acid | 10 mL |
| | Filtered water | 730 mL |
| | *Guatteria citriodora* Ducke oil | 2.5 mL |
| | *Protium heptaphyllum* March oil | 2.5 mL |
| Phase B | Amphoteric betaines | 30 mL |

EXAMPLE 9

Formulation for Liquid Disinfectant

The liquid disinfectant based on oils with bactericidal and fixing properties uses essential oils of *Guatteria citriodora* Ducke as antimicrobial and from *Aniba roseodora* Ducke as fixing of the disinfectant effect. It helps in the cleaning process preventing the occurrence of bacterial diseases in hospitals, clinics and laboratories. It is not toxic to human skin when used in continuous form.

TABLE 13

Oil based disinfectant

| | |
|---|---|
| *Guatteria citriodora* Ducke oil | 2.5% |
| Ethoxilated nonylphenol with 10EO | 3.0% |
| Butyldiglycol | 2.0% |
| Alkyl dimethyl benzyl ammonium chloride (50%) | 2.5% |
| *Aniba roseodora* Ducke oil | 0.2% |
| Colouring indicator | qs |
| Filtered water | To 100 |

EXAMPLE 10

Formulation for Prophylatic Spray

In this embodiment, the purpose of the formulation is to fix in the skin, through the constituents of *Aniba roseodora* Ducke oil in a fast and practical way, the antimicrobial properties of the *Guatteria citriodora* Ducke oil and the wound healing property of the *Protium heptaphyllum* March oil. The final product of this association in the antimicrobial and wound healing spray form is directed to bandages in skin wounds.

In a special embodiment of the present invention, the formulation for prophylatic spray with the essential oils comprises the compounds according to the following Table 14.

TABLE 14

Prophylatic antimicrobial and wound healing spray

| | |
|---|---|
| Glycerin | 30 mL |
| Ethanol | 0.3% |
| *Aniba roseodora* Ducke oil | 0.1 mL |
| *Guatteria citriodora* Ducke oil | 0.02 mL |
| *Protium heptaphyllum* March oil | 0.05 mL |
| Saline solution | To 1 mL |

EXAMPLE 11

Disinfectant of Toothbrushes, Dental Prosthesis and Orthodontic Retainers

This invention purposes to disinfect toothbrushes and dental prosthesis through the components of *Cyperus rotundus* Linn oil with biofilm remover property by the removal of the biofilm caused by *Streptococcus mutans*, the main bacteria that causes the dental caries in humans and the *Guatteria citriodora* Ducke oil with antimicrobial and antiseptic property against oral bacteria and the *Protium heptaphyllum* March oil that presents antimicrobial action. The final product of this association in the form of a disinfectant is directed to the cleaning of brushes and dental prosthesis and orthodontic retainers, in the gingival disease prevention and the dental caries formation.

In a special embodiment of the present invention, the formulation for disinfectant of brushes, dental prosthesis and orthodontic retainers comprising the compounds according to the following Table 15.

TABLE 15

Disinfectant of toothbrushes, dental prosthesis and orthodontic retainers

| | |
|---|---|
| Cetylpyridinium chloride | 100 mg |
| Citric acid | 100 mg |
| *Cyperus rotundus* Linn oil | 0.1 mL |
| *Guatteria citriodora* Ducke oil | 0.02 mL |
| *Protium heptaphyllum* March oil | 0.05 mL |
| Polysorbate 60 | 0.3 mL |
| Ethanol 95% | 10 mL |
| Sorbitol solution 70% | 20 mL |
| Hydrogen peroxide 10 vol | To 100 mL |

The skilled in the art will understand the teachings of the present invention and know that small changes in the embodiments herein presented must be understood as being within the spirit of the invention and within the scope of the following claims.

The invention claimed is:

1. A phytocosmetic and/or phytotherapeutic formulation comprising at least one essential oil of a plant selected from the group consisting of *Protium heptaphyllum, Guatteria citriodora, Cyperus rotundus*, and combinations thereof in the form of a phytotherapic dental gel comprising:
   a) at least one essential oil from the plant selected from the group consisting of *Protium heptaphyllum, Guatteria citriodora, Cyperus rotundus* in the range from 0.02% w/w to 0.1% w/w;
   b) at least one surfactant agent in the range of from 0.8% w/w to 1.5% w/w;
   c) at least one thickening agent in the range from 0.3% w/w to 0.7% w/w;
   d) at least one humectant agent in the range from 20% w/w to 25% w/w;
   e) at least one abrasive agent in the range from 45% w/w to 50% w/w;
   f) at least one antimicrobial agent in the range from 0.02% w/w to 0.5% w/w;
   g) at least one biofilm removing agent in the range from 0.05% w/w to 0.15% w/w; and
   h) at least one fluor based compound in the range from 900 ppm to 1100 ppm.

2. The phytocosmetic and/or phytotherapeutic formulation according to claim 1, wherein the at least one humectant agent is selected from the group consisting of:
   a) a water-soluble liquid polyols selected from the group consisting of glycerin, propylene glycol, hexylene glycol, buylene glycol, dipropylene glycol, and combinations thereof;
   b) a polyethylene glycol of the formula: HO—(RO)$_n$-H, wherein R is an alkyl group with 2 or 3 carbon atoms and n is 2 to 10;
   c) methyl glycosides polyethylene glycol ethers;
   d) urea; and
   e) mixtures thereof.

3. The phytocosmetic and/or phytotherapeutic formulation according to claim 1, wherein the at least one thickening agent is selected from the group consisting of carboxylic acid/carboxylate copolymers, hydrophobically-modified cross-linked copolymers of carboxylic acid and alkyl carboxylate vinyl polymers, cross linked acrylic acid polymers, methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and combinations thereof.

4. The phytocosmetic and/or phytotherapeutic formulation according to claim 1, wherein the at least one surfactant agent is selected from the group consisting of an anionic surfactant, a non-ionic surfactant, a cationic surfactant, an amphoteric/zwitterionic surfactant and combinations thereof.

5. The phytocosmetic and/or phytotherapeutic formulation according to claim 4, wherein the anionic surfactant agent is selected from the group consisting of alkaline earth metals salts of fatty acids, alkaline earth metals salts of fatty acids, alkyl sulfates ammonium salts, ethoxylated alkyl sulfates, alkyl sulfonates, alkylaryl sulfonates, alkyl sulfosuccinate, alkyl ether sulfosuccinate, alkyl sulfosuccinamate, alkyl amide sulfosuccinate, alkyl succinate, alkyl carboxylate, alkyl ether carboxylate comprising a carbonic chain from 12 to 20 carbon atoms and an aryl group comprising a phenyl or benzyl group, and combinations thereof.

6. The phytocosmetic and/or phytotherapeutic formulation according to claim 4, wherein the non-ionic surfactant agent is selected from the group consisting of ethoxylated alcohols with linear alcohol groups with from 12 to 18 carbon atoms and from 2 to 8 ethylene oxide (EO) by mol of alcohol; fatty alcohols with more than 12 EO; alkyl glycosides of the general formula RO(G)x, wherein R means a primary linear or methyl branched, aliphatic group with from 8 to 22 carbon atoms, G is an glycosidic unit containing from 5 to 6 carbon atoms, and in which the oligomerization degree x, is a number between 1 and 10; propoxylated fatty acids alkyl esters with 1 to 4 carbon atoms in the alkyl chain; amine oxide N-cocoalkyl-N, N-dimethylamine oxide; N-tallow alkyl-N,N-dihydroxyethylamine oxide and fatty acids alkanolamides; and combinations thereof.

7. The phytocosmetic and/or phytotherapeutic Formulation according to claim 4, wherein the amphotheric/zwiterionic surfactant agent is selected from the group consisting of amphocarboxylate compounds, alkyl betaines, amidoalkyl betaines, amidoalkyl sultaines, amphophosphates, phosphobetaines secondary and tertiary amines derivatives or quaternary ammonium derivatives, quaternary phosphonium derivatives or tertiary compounds of sulfonium, and combinations thereof.

8. The phytocosemtic and/or phytotherapeutic formulation according to claim 1, wherein the antimicrobial agent is selected from the group consisting of tertiary amines with a fatty alkyl group of 12 to 18 carbon atoms, tertiary amines with a fatty alkyl group of 12 to 18 carbon atoms with two (poly)oxyethylenes attached to the nitrogen, quaternary ammonium compounds, benzethonium chloride, dodecyl-, tetradecyl- and hexadecyltrimethyl ammonium halides, methylparaben, ethylparaben, butylparaben, propylparaben isobutylparaben, plants selected from the genus *Guatteria*, plants selected from the genus *Protium*, plants selected from the genus *Cyperus*, and combinations thereof.

9. The phytocosmetic and/or phytotherapeutic formulation according to claim 1, wherein the at least one abrasive agent is selected from the group consisting of pomme stone, alumina, silica, alkaline and alkaline earth metal phosphate, carbonates salts, silicates salts, calcium pyrophosphate, calcium phosphate, alkali metal metaphosphates, magnesium phosphates, magnesium silicate, calcium meta silicate, and combinations thereof.

10. The phytocosmetic and/or phytotherapeutic formulation according to claim 1, wherein the at least one fluor based compound is selected from the group consisting of sodium monofluorophosphate, lithium monofluorophosphate, potassium monofluorophosphate, ammonium monofluorophosphate, sodium fluorides, potassium fluorides, and combinations thereof.

11. The phytocosmetic and/or phytotherapeutic formulation according to claim 1, wherein the at least one biofilm removing agent is a vegetal extract in the form of an essential oil from a plant that belongs to genus *Cyperus*.

12. The phytocosmetic and/or phytotherapeutic formulation according to claim 1, further comprising at least one of a flavoring agent, an enzyme, a fragrance, a pigment, a colorant, a preservative, a pH regulator, a propellant, an antioxidants, a chelant, a bactericide, a fungicide, an antiviral agent, an opacifying agent, a bleach agent, a conditioning polymer, silicone, and combinations thereof.

13. The phytocosmetic and/or phytotherapeutic formulation according to claim 6, wherein the aliphatic group has from 12 to 18 carbon atoms.

14. The phytocosmetic and/or phytotherapeutic formulation according to claim 8, wherein the plants selected from the genus *Guatteria*, the plants selected from the genus *Protium*, and the plants selected from the genus *Cyperus* are *Guatteria citriodora* Ducke, *Protium heptaphyllum* March, and *Cyperus rotundus* Linn, respectively, and combinations thereof.

15. The phytocosmetic and/or phytotherapeutic formulation according to claim 11, wherein the plant that belongs to genus *Cyperus* is *Cyperus rotundus* Linn.

16. A phytocosmetic and/or phytotherapeutic formulation comprising at least one essential oil from the plant *Protium heptaphyllum*, wherein the formulation is in the form of a phytotherapic dental gel comprising:
a) the at least one essential oil from the plant *Protium heptaphyllum* is in the range from 0.02% w/w to 0.1% w/w;
b) at least one surfactant agent in the range from 0.8% w/w to 1.5% w/w;
c) at least one thickening agent in the range from 0.3% w/w to 0.7% w/w;
d) at least one humectant agent in the range from 20% w/w to 25% w/w;
e) at least one abrasive agent in the range from 45% w/w to 50% w/w;
f) at least one antimicrobial agent in the range from 0.02% w/w to 0.5% w/w;
g) at least one biofilm removing agent in the range from 0.05% w/w to 0.15% w/w; and
h) at least one fluor based compound in the range from 900 ppm to 1100 ppm.

* * * * *